United States Patent
Chantz

(10) Patent No.: US 10,215,736 B2
(45) Date of Patent: Feb. 26, 2019

(54) ACOUSTIC MONITOR FOR POWER TRANSMISSION LINES

(71) Applicant: International Business Machines Corporation, Armonk, NY (US)

(72) Inventor: Hyman D. Chantz, Scarsdale, NY (US)

(73) Assignee: International Business Machines Corporation, Armonk, NY (US)

( * ) Notice: Subject to any disclaimer, the term of this patent is extended or adjusted under 35 U.S.C. 154(b) by 465 days.

(21) Appl. No.: 14/921,649

(22) Filed: Oct. 23, 2015

(65) Prior Publication Data
US 2017/0115256 A1    Apr. 27, 2017

(51) Int. Cl.
| | | |
|---|---|---|
| G01F 17/00 | (2006.01) |
| G01F 23/00 | (2006.01) |
| G01L 7/00 | (2006.01) |
| G01N 11/00 | (2006.01) |
| G01N 29/46 | (2006.01) |

(Continued)

(52) U.S. Cl.
CPC ............. *G01N 29/46* (2013.01); *G01N 29/38* (2013.01); *G01R 31/085* (2013.01); *G01R 31/088* (2013.01); *G01R 31/1209* (2013.01); *G01N 2291/023* (2013.01); *G01N 2291/0289* (2013.01)

(58) Field of Classification Search
CPC .. G01N 29/46; G01N 29/38; G01N 2291/023; G01N 2291/0289; G01R 31/088; G01R 31/085; G01R 31/1209; G01H 1/003; G01H 1/00; G01F 1/667; G01F 1/74; G01F 1/8436; G01F 15/024; B65H 23/0204; B65H 2553/30
See application file for complete search history.

(56) References Cited

U.S. PATENT DOCUMENTS 4,818,990 A * 4/1989 Fernandes .............. G01R 15/14
340/12.32
4,904,996 A * 2/1990 Fernandes ............ G01R 15/142
340/601

(Continued)

OTHER PUBLICATIONS

English Translation of Japanese patent JP3104711B2, Oct. 30, 2000.

(Continued)

*Primary Examiner* — Mohamed Charioui
*Assistant Examiner* — Leonard S Liang
(74) *Attorney, Agent, or Firm* — Martin & Associates, LLC; Derek P. Martin

(57) ABSTRACT

An acoustic monitor detects and logs events based on the acoustic characteristics of the event. The acoustic monitor is placed on a power transmission tower, and a baseline acoustic signature is established. Events can be defined by variance from the baseline, or by matching one of a set of predefined acoustic signatures. When an event is detected, the acoustic monitor logs the event. A repair person queries the acoustic monitors to narrow down where the event occurred to be between two towers, and can then query the acoustic monitors on those two towers. Using the timestamps of the event in each of the towers, and using the known speed of sound in air, the repair person can quickly calculate the location of the event from both towers. By knowing the location of the event, the repair person knows exactly how to quickly access the location to make the needed repairs.

3 Claims, 9 Drawing Sheets

(51) Int. Cl.
*G01R 31/08* (2006.01)
*G01N 29/38* (2006.01)
*G01R 31/12* (2006.01)

(56) References Cited

U.S. PATENT DOCUMENTS

| | | | |
|---|---|---|---|
| 6,082,193 A | 7/2000 | Paulson | |
| 6,348,856 B1* | 2/2002 | Jones | G01S 5/14 |
| | | | 340/10.1 |
| 2001/0012129 A1* | 8/2001 | Inoue | H04N 1/4051 |
| | | | 358/2.1 |
| 2002/0037732 A1* | 3/2002 | Gous | G01S 5/0063 |
| | | | 455/502 |
| 2002/0154372 A1* | 10/2002 | Chung | H04B 10/0775 |
| | | | 398/187 |
| 2002/0191705 A1* | 12/2002 | Melsa | H04L 27/2624 |
| | | | 375/295 |
| 2003/0123701 A1* | 7/2003 | Dorrell | G06F 21/64 |
| | | | 382/100 |
| 2003/0198304 A1* | 10/2003 | Sugar | G01R 13/0254 |
| | | | 375/340 |
| 2004/0100868 A1* | 5/2004 | Patterson, Jr. | F41H 11/00 |
| | | | 367/127 |
| 2004/0111227 A1* | 6/2004 | Stein | G06F 17/142 |
| | | | 702/77 |
| 2004/0143397 A1 | 6/2004 | Paulson et al. | |
| 2004/0148057 A1* | 7/2004 | Breed | B60Q 9/008 |
| | | | 700/242 |
| 2004/0192345 A1* | 9/2004 | Osborn | G01S 5/0036 |
| | | | 455/456.1 |
| 2007/0088546 A1* | 4/2007 | Song | G10L 19/265 |
| | | | 704/233 |
| 2007/0258526 A1* | 11/2007 | Urvas | H03H 17/0213 |
| | | | 375/260 |
| 2008/0219100 A1* | 9/2008 | Fisher | F41H 11/00 |
| | | | 367/124 |
| 2008/0317260 A1* | 12/2008 | Short | G10L 21/02 |
| | | | 381/92 |
| 2009/0182524 A1* | 7/2009 | Stephanson | G06K 9/00771 |
| | | | 702/127 |
| 2010/0271199 A1* | 10/2010 | Belov | G01M 5/00 |
| | | | 340/539.3 |
| 2011/0055669 A1* | 3/2011 | DeHaan | G06F 11/0709 |
| | | | 714/799 |
| 2012/0327745 A1* | 12/2012 | Yardibi | G01S 3/80 |
| | | | 367/121 |
| 2014/0260638 A1* | 9/2014 | Hood | G01N 29/14 |
| | | | 73/647 |
| 2015/0022352 A1* | 1/2015 | Gettings | G01N 21/84 |
| | | | 340/540 |
| 2015/0339919 A1* | 11/2015 | Barnett | G08G 1/0116 |
| | | | 340/907 |
| 2016/0147209 A1* | 5/2016 | Stoupis | G01R 31/40 |
| | | | 700/295 |

OTHER PUBLICATIONS

English Translation of Japanese patent JP3217205B2, Oct. 9, 2001.

* cited by examiner $$A = |TS1 - TS2| \times 343 \text{ m/s}$$

$$\text{Distance from Tower to Event} = \frac{\text{Distance Between Towers} - A}{2}$$

ACOUSTIC MONITOR FOR POWER TRANSMISSION LINES

BACKGROUND

1. Technical Field

This disclosure generally relates to power distribution systems, and more specifically relates to a way to detect a failure in power transmission lines.

2. Background Art

High-voltage power transmission lines often span long distances between towers. These transmission lines and their towers may be located in remote areas. In addition, towers in some areas, such as mountainous areas, may make access to the power lines and towers difficult for making needed repairs.

Power transmission lines can fail due to several different types of events. An ice storm can deposit so much ice on a power transmission line that the additional weight of the ice causes the power transmission line to break. A vandal or saboteur can cause a power line to break by placing a conductor, such as a chain or metal bar, on a power transmission line to create a short to ground or between power transmission lines. The high current created by such a short can create sufficient heat that can cause a power transmission line to break. In addition, a power transmission line could have a manufacturing defect that causes the power transmission line to break.

Regardless of the cause, when a power transmission line breaks, there is a need to quickly identify the location of the break and make needed repairs to restore power to those who lost power due to the break. For power transmission lines that span tens or hundreds of kilometers, it is not a simple thing for a repair person to ascertain where the power line broke. Thus, it may take manual inspection of the power transmission lines for a considerable period of time over a considerable distance before the repair person can identify the location of the break in a power transmission line. This can lead to considerable delays in getting the needed repairs made so the power is restored.

SUMMARY

An acoustic monitor detects and logs events based on the acoustic characteristics of the event. The acoustic monitor is placed on a tower, and a baseline acoustic signature is established. Events can be defined by variance from the baseline, or by matching one of a set of predefined acoustic signatures. When an event is detected, the acoustic monitor logs the event. A repair person queries the acoustic monitors to narrow down where the event occurred to be between two towers, and can then query the acoustic monitors on those two towers. Using the timestamps of the event in each of the towers, and using the known speed of sound in air, the repair person can quickly calculate the location of the event from both towers. By knowing the location of the event, the repair person knows exactly how to quickly access the location to make the needed repairs.

The foregoing and other features and advantages will be apparent from the following more particular description, as illustrated in the accompanying drawings.

BRIEF DESCRIPTION OF THE DRAWING(S)

The disclosure will be described in conjunction with the appended drawings, where like designations denote like elements, and:

DETAILED DESCRIPTION

The disclosure and claims herein relate to an acoustic monitor that detects and logs events based on the acoustic characteristics of the event. The acoustic monitor is placed on a tower, and a baseline acoustic signature is established. Events can be defined by variance from the baseline, or by matching one of a set of predefined acoustic signatures. When an event is detected, the acoustic monitor logs the event. A repair person queries the acoustic monitors to narrow down where the event occurred to be between two towers, and can then query the acoustic monitors on those two towers. Using the timestamps of the event in each of the towers, and using the known speed of sound in air, the repair person can quickly calculate the location of the event from both towers. By knowing the location of the event, the repair person knows exactly how to quickly access the location to make the needed repairs.

Figure 1:
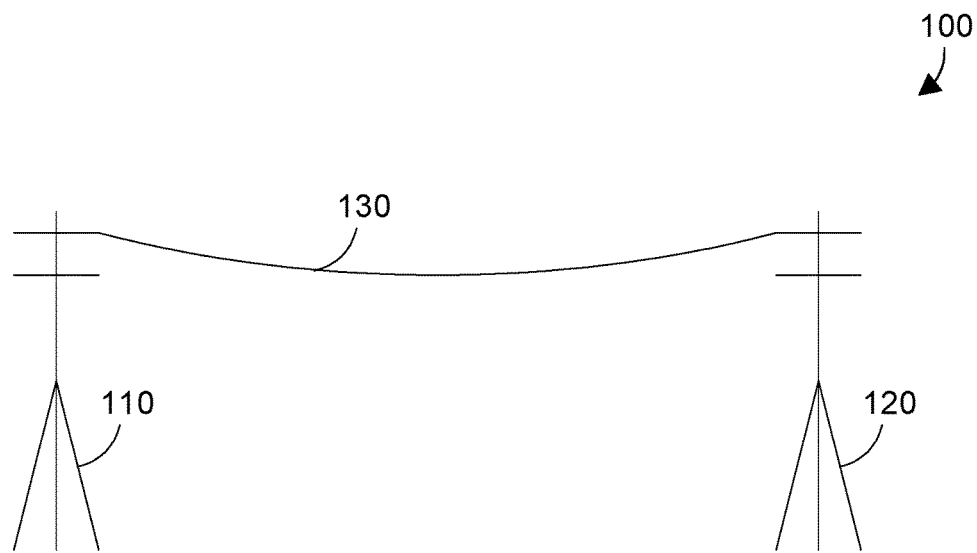
FIG. 1 is a diagram of a power transmission system that includes a power transmission line running between two towers.
Figure 2:
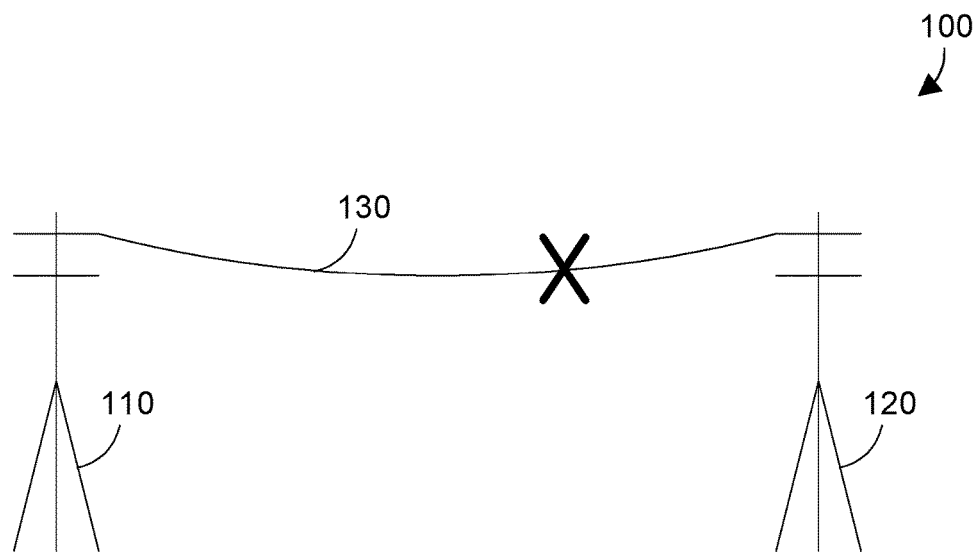
FIG. 2 is a diagram of the power transmission system in FIG. 1 with a break in the power transmission line represented by the X.

FIG. 1 represents a power transmission system 100 that includes two towers 110 and 120 with a power transmission line 130 between the two. Note the transmission line beyond the two towers is not shown in FIG. 1. When the transmission line breaks, as shown in FIG. 2 at the X, the repair person needs to be able to quickly determine where the break occurred so the break can be repaired in a timely manner.

Figure 3:
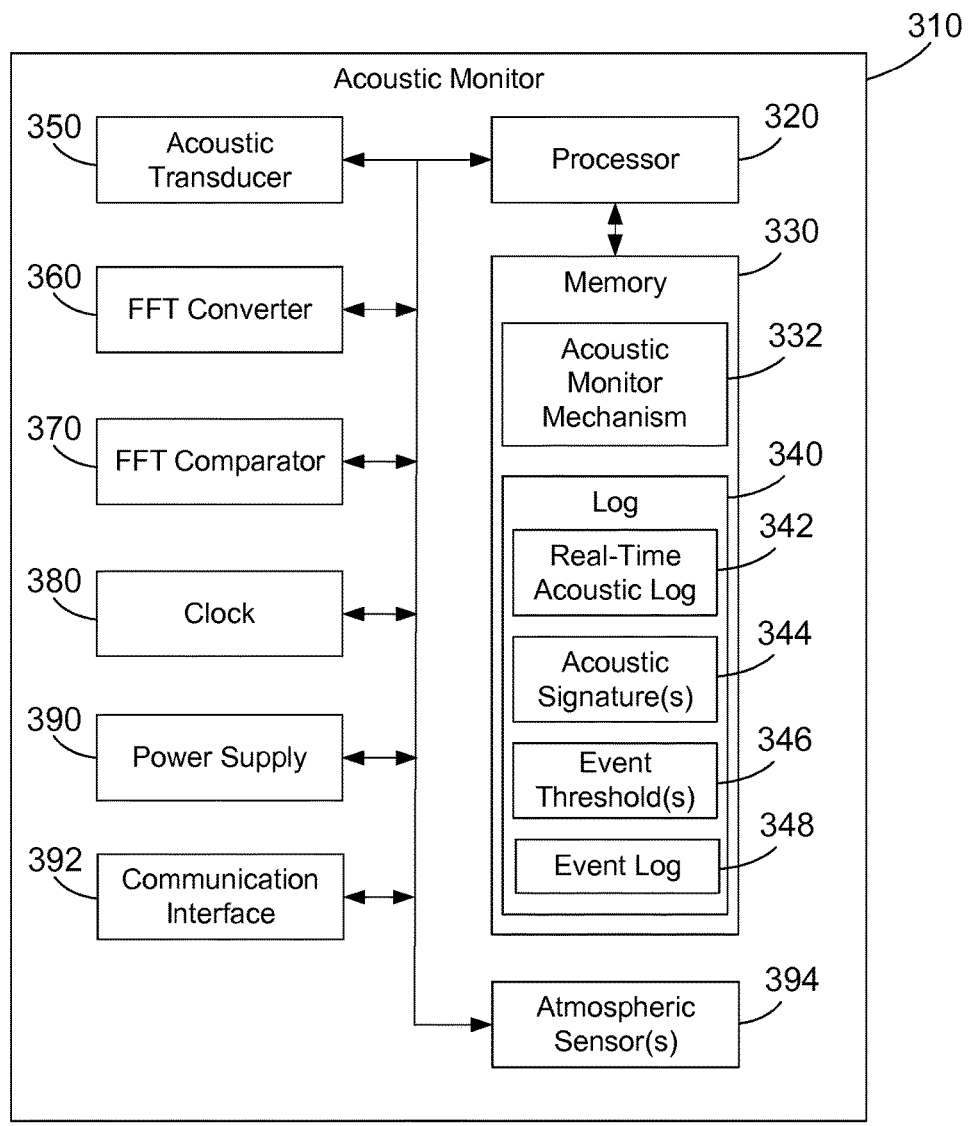
FIG. 3 is a block diagram of an acoustic monitor that detects events for power transmission lines.

Referring to FIG. 3, an acoustic monitor 310 can be placed at or near towers for power transmission lines. The acoustic monitor 310 includes a processor 320, a memory 330, an acoustic transducer 350, a Fast Fourier Transform (FFT) converter 360, an FFT comparator 370, a clock 380, a power supply 390, a communication interface 392, and may optionally include one or more atmospheric sensors 394. The processor 320 may be constructed from one or more microprocessors and/or integrated circuits. Processor 320 executes program instructions stored in memory 330. Memory 330 stores programs and data that processor 320 may access. Memory 330 may include any suitable combination of different memory types. For example, memory 330 could include dynamic random access memory (DRAM) that has a relatively small size and a fast access time and could also include non-volatile memory (NVRAM) that has a much larger size and a slower access time. Programs stored in NVRAM could then be loaded into the DRAM in order to be executed by the processor 320. This simple example shows the memory 330 can include any suitable number and type of memories in any suitable hierarchy, whether currently known or developed in the future.

One suitable implementation for processor 320 is a microcontroller. Another suitable implementation for processor 320 is a state machine. Yet another suitable implementation for processor 320 is a digital signal processor. Still another suitable implementation for processor 320 is a neuromorphic processor. Processor 320 as disclosed herein expressly extends to any suitable combination of hardware and/or software that allow performing the functions described herein.

Memory 330 preferably includes an acoustic monitor mechanism 332 and a log 340 that includes a real-time acoustic log 342, one or more acoustic signatures 344, one or more event thresholds 346, and an event log 348. The acoustic monitor mechanism 332 is software executed by the processor 320 that causes the acoustic monitor 310 to perform the functions disclosed herein. The real-time acoustic log 342 can include raw acoustic data from the acoustic transducer 350, and/or can include the FFT results of the FFT converter 360 analyzing the raw data from the acoustic transducer 350. The real-time acoustic log 342 is most preferably a continuously-running log, where the oldest data is being replaced by the newest data. The size of the real-time acoustic log 342 can be designed according to specific needs. For example, when the acoustic monitor 310 is placed on a tower at a location that is easily accessible, the real-time acoustic log 342 could record, for example, twelve hours of data. This would give the repair person access to the past twelve hours of acoustic data, which assumes a repair person can be on-site in less than twelve hours. In another example, when the acoustic monitor 310 is placed on a tower at a location that is inaccessible, the real-time acoustic log 342 could record, for example, 36 hours of acoustic data. These examples of 12 and 36 hours are simply examples, and the recording capacity of the real-time acoustic log 342 could be substantially longer or shorter, as needed. For example, the real-time acoustic log 342 could include sufficient capacity to record data for a week, or a month. Note that some of the data in the real-time acoustic log 342 could be copied to an event log 348 to create a permanent record of the event, as described in more detail below.

The acoustic signatures 344 include a baseline audio signature, and optionally may also include one or more acoustic signatures that characterize different types of events. This is discussed in more detail below with reference to FIG. 6. The event threshold(s) 346 include one or more thresholds that determine when an event has occurred. For example, a single event threshold could be specified as a percentage or other predefined criteria such that any FFT that varies from a baseline FFT more than the specified percentage or predefined criteria will be tagged as an event. An event threshold 346 can include any suitable number, calculation, heuristic, or other method for determining when an event has occurred. The event log 348 includes logged events that were detected by the acoustic monitor mechanism 332 based on the event threshold(s) 346. The event log 348 includes a timestamp for each event, and may additionally include any suitable event data, including raw acoustic data from the acoustic transducer 350 before and after the events, FFT data before and after the events, etc. The data logged for an event in event log 348 most preferably includes data before and after the occurrence of an event. Thus, when an event is detected, an entry in the event log 348 is made for the event, and any suitable amount of data before and after the event is logged as well. For example, if a power line breaks, and the break is detected as an event by the acoustic monitor mechanism 332, the break could be logged as an event 348 in log 340 along with the raw audio data from the acoustic transducer 350 ten seconds before the break and ten seconds after the break. This would allow a repair person to actually listen to the audio record of the break. Similarly, FFT data before and after the event can be logged with an event. The disclosure and claims herein expressly extend to logging any suitable amount of data before and/or after an event when the event is logged.

The acoustic transducer 350 is any transducer suitable for detecting vibrations in the acoustic frequency range, such as a microphone. Note that "acoustic frequency range" here includes sounds that are audible to a human ear, and additionally includes sounds of lower frequency and higher frequency than are audible by the human ear. The acoustic transducer 350 detects acoustic vibrations. For example, the acoustic transducer 350 can detect the noise of a power line breaking, or sound or other vibrations from other events. Data from the acoustic transducer 350 can be logged in real-time to the real-time acoustic log 342.

The FFT converter 360 receives the signal from the acoustic transducer 350 and takes a spectrogram of this information by converting the amplitude information from the acoustic transducer 350 into corresponding frequency information. Data from the FFT converter 360 may be logged in the real-time acoustic log 342. The FFT comparator 370 compares two FFTs generated by the FFT converter 360 to determine whether an event has occurred. The FFT comparator 370 can function according to defined event thresholds 346. For example, an event threshold of 20% could be specified, which means when an FFT has more than 20% variance with a prior FFT, such as an FFT for a baseline acoustic signature, the FFT comparator will determine an event has occurred. The FFT converter 360 and FFT comparator 370 could be hardware, such as suitable special-purpose processors, or could be software executed by processor 320 or executed by a special-purpose processor, such as a math co-processor. The detection of an event by the acoustic monitor mechanism 332 using the FFT comparator 370 results in logging the event 348 and any associated information relating to the event in the event log 348.

The clock 380 is most preferably a Coordinated Universal Time (UTC) clock. A coordinated universal time clock is used because each acoustic monitor needs to have its clock synchronized with the clocks of all other acoustic monitors. By making the clocks in each acoustic monitor a coordinated universal time clock, the timestamps of events in different acoustic monitors can be compared. The coordinated universal time clock could be derived from any suitable source, including global positioning system (GPS) satellites, cell phone towers, WWVB transmission, by accessing a time reference website, etc.

The power supply 390 provides the power needed for the acoustic monitor 310. Power supply 390 can supply the needed power from any suitable power source, including a direct current (DC) source such as one or more batteries, or an alternating current (AC) source such as line power. Due to the proximity to power transmission lines on a tower, one option is to have the power supply 390 include an inductive coupler that provides the needed power directly from the power transmission lines.

The communication interface 392 may include any suitable interface that allows an external device to communicate with the acoustic monitor 310 and retrieve data from the event log 348 from the acoustic monitor 310. Additional details regarding the communication interface 392 are provided below with respect to FIG. 14.

One or more atmospheric sensors 394 can optionally be included when accuracy of the location of the break is important. One skilled in the art will appreciate that the speed of sound in air varies as a function of barometric pressure and temperature. When the location can be determined without a need to be extremely accurate, a speed of 343 meters per second (m/s) can be used. But when the location needs to be more exact, the atmospheric sensors 394 can provide atmospheric and temperature data that allow more accurately calculating the speed of sound in air under the precise weather conditions that existed when the event occurred, which, in turn, allows calculating the location of the event with more precision.

Figure 4:
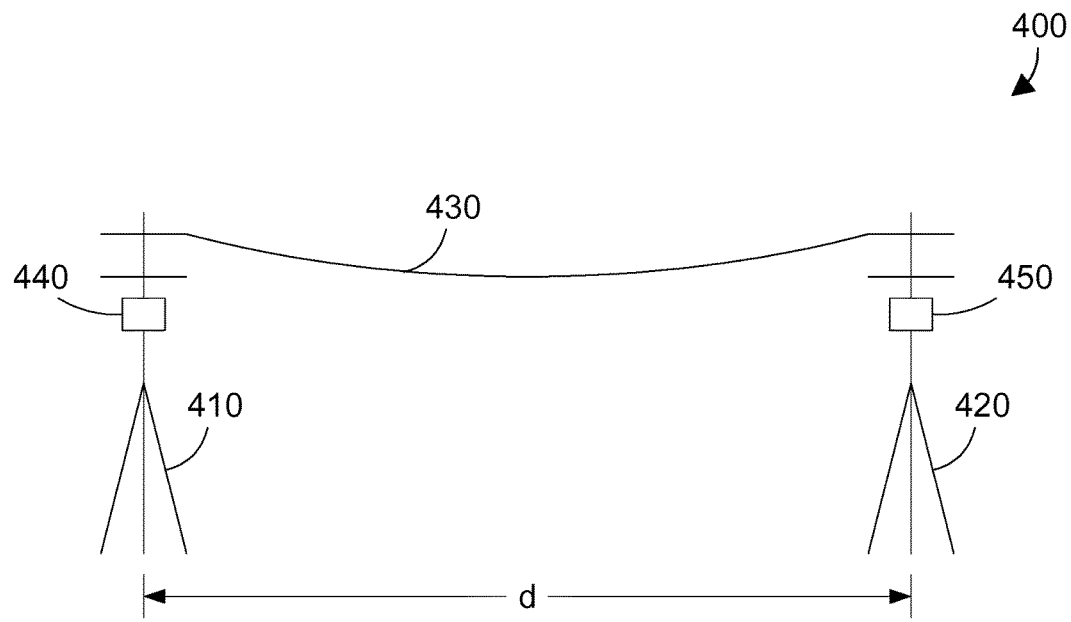
FIG. 4 is a diagram showing a power transmission system similar to that in FIG. 1 but equipped with acoustic monitors such as shown in FIG. 3 on each tower.

Referring to FIG. 4, a power transmission system 400 includes two towers 410 and 420 with a power transmission line 430 running between the two. The towers are separated by a distance d. Tower 410 includes a first acoustic monitor 440, and tower 420 includes a second acoustic monitor 450. Acoustic monitors 440 and 450 are preferably the acoustic monitor 310 shown in FIG. 3. By placing acoustic monitors on the towers, the location of an event between the two towers can be easily determined by comparing timestamps of the events at the two towers, as discussed in more detail below.

Figure 5:
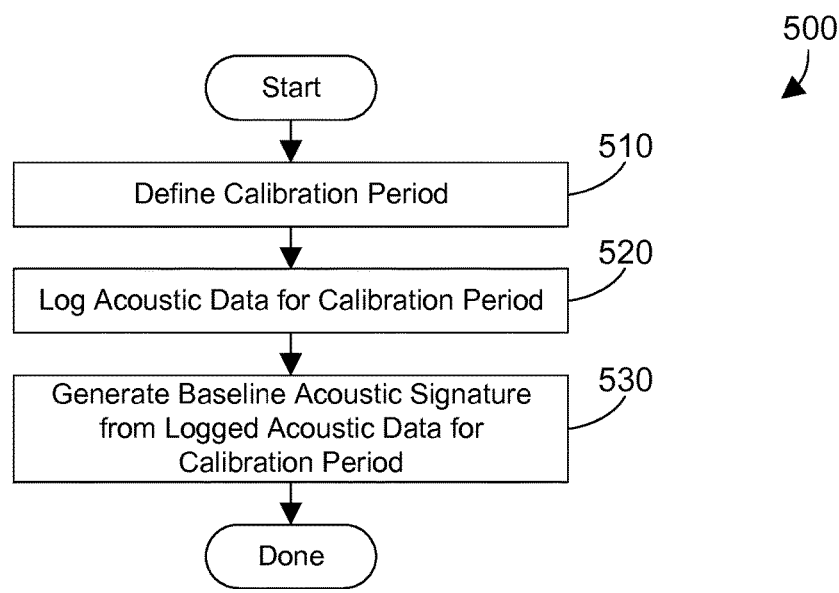
FIG. 5 is flow diagram of a method generating a baseline acoustic signature for the acoustic monitor in FIG. 3.

For the acoustic monitor to detect events, a baseline is first established under normal conditions. Referring to FIG. 5, method 500 is preferably performed by the acoustic monitor mechanism 332 in FIG. 3. A calibration period is defined (step 510). The calibration period can be any suitable time period, from seconds to days. Acoustic data is then logged for the calibration period (step 520). A baseline acoustic signature is then generated from the acoustic data for the calibration period (step 530). Method 500 is then done. The baseline acoustic signature is stored as an acoustic signature 344 in FIG. 3.

Figure 6:
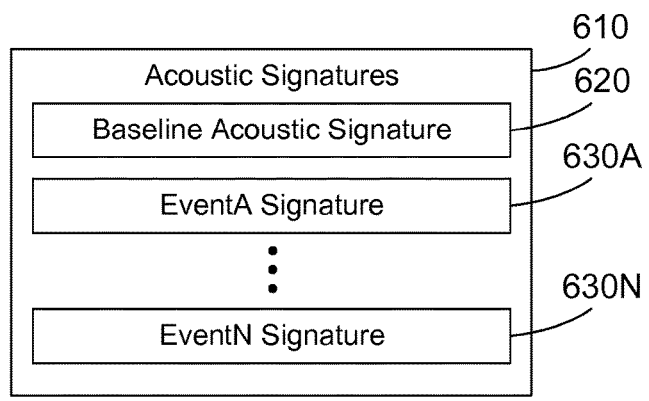
FIG. 6 is a block diagram that shows one particular implementation for the acoustic signature(s) 344 shown in FIG. 3.

Referring to FIG. 6, acoustic signatures 610 represent one suitable implementation for acoustic signature(s) 344 in FIG. 3. Acoustic signatures 610 include a baseline acoustic signature 620 and one or more event signatures 630A, . . . , 630N. Event signatures may be characterized as a function of raw data from the acoustic transducer 350 or as a function of FFT data from the FFT converter 360. For example, a break may have specific characteristics that allow creating a "break event signature" such that when the current conditions satisfy the "break event signature", the acoustic monitor mechanism 332 knows a break event just happened. In addition, event signatures 630A, . . . , 630N could include a library of different event signatures that are programmed into the acoustic monitor so the acoustic monitor can detect events based on the library of event signatures without ever having detected one of those events before. Any suitable mechanism and method can be used to compare current conditions to an event signature, whether currently known or developed in the future.

Figure 7:
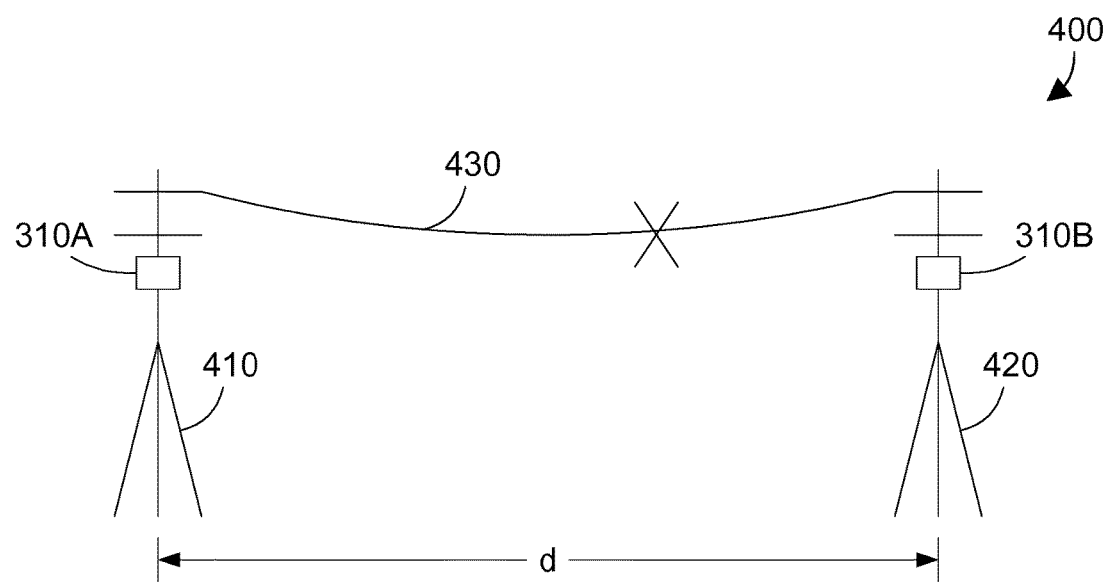
FIG. 7 is a diagram showing the power transmission system in FIG. 4 with a break in the power transmission line represented by the X.

Referring to FIG. 7, with the power transmission system 400 shown in FIG. 4, we now assume a break happens at a point marked with the X in FIG. 7. Using the logged event information, the location of the break can be determined by a repair person as discussed below. Acoustic monitors 310A and 310B in FIG. 7 represent two different instances of acoustic monitor 310 shown in FIG. 3.

Figure 8:
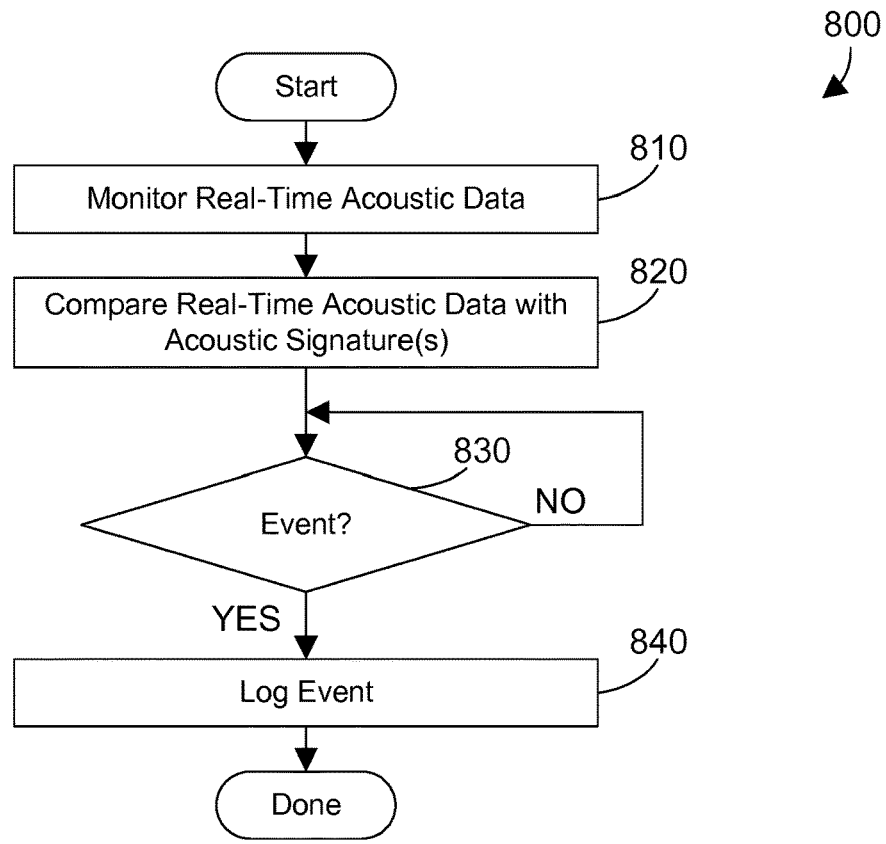
FIG. 8 is a flow diagram of a method for the acoustic monitor to detect and log an event.

FIG. 8 shows a method 800 that is preferably performed by the acoustic monitor mechanism 332 in FIG. 3. Real-time acoustic data is monitored (step 810). The real-time acoustic data monitored in step 810 can include raw acoustic data from the acoustic transducer 350, and/or can include FFT data from the FFT converter 360. The real-time acoustic data is compared with one or more acoustic signatures (step 820). As long as no event is detected (step 830=NO), method 800 loops back to step 830 until an event is detected (step 830=YES), at which point the event is logged (step 840). The logging of the event in step 840 can include logging the timestamp of the event along with logging any other suitable information relating to the event, such as acoustic data before and after the event.

Figure 9:
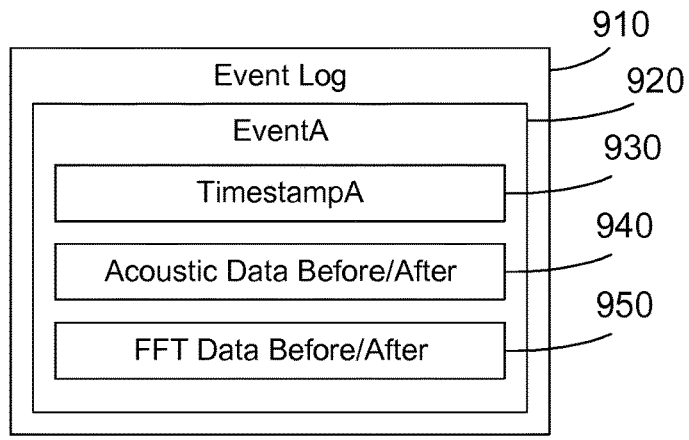
FIG. 9 is a block diagram that shows one particular implementation for the event log 348 shown in FIG. 3.

One specific implementation of the event log 348 shown in FIG. 3 is event log 910 shown in FIG. 9, which shows a log for a single event EventA 920. EventA 920 has been detected and logged in the event log 910. The logged data for EventA 920 includes a timestamp of the event 930, and may additionally include acoustic data before and/or after the event 940, and/or FFT data before and/or after the event 950.

Figure 10:
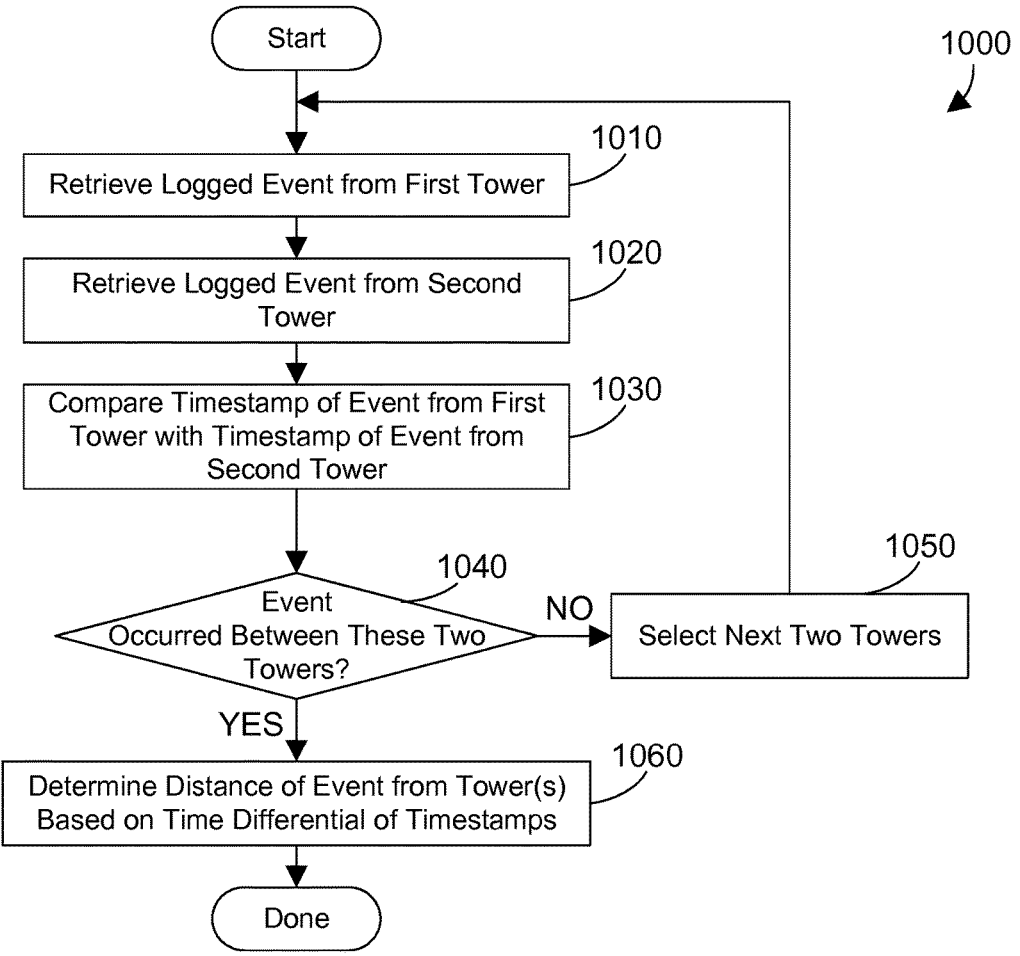
FIG. 10 is a flow diagram of a method for determining location of an event based on time differential of timestamps corresponding to the event from two towers.

Once an event has been detected and logged as shown in FIG. 9, the logged event data can be used to determine the location of the event. This is done by reading the logged event data from the two towers between which the event occurred. Method 1000 in FIG. 10 is discussed with reference to the specific example in FIG. 11. In this example, a break of the power transmission line has occurred between tower T3 and tower T4 in FIG. 11. Each tower T1, T2, T3 and T4 have an acoustic monitor such as 310 shown in FIG. 3 even though they are not explicitly shown in FIG. 11. We assume the break was detected as an event by the acoustic monitors in towers T2, T3 and T4, but it was not detected as an event by tower T1 because it is too far away, with the result that the sound or vibrations that reached tower T1 were not enough to trigger the logging of the event by the acoustic monitor on tower T1. We assume a repair person goes first to tower T1 in FIG. 11, perhaps because this is the first tower in the line. We assume for this simple example in FIG. 11 the repair person queries the acoustic monitor on tower T1 and discovers that tower T1 did not record any event that would correspond to the break event. This is easily done because the time when the power went down is typically logged by the power company systems, so the repair person can simply look for event data just before and after the time the power went down. The absence of a logged event corresponding to the time of the break causes the repair person to move to tower T2 and query the acoustic monitor on tower T2. Because T2 detected the break as an event, it will have it its log the event data, which includes the timestamp of the event. The logged event is retrieved from tower T2 in step 1010 in FIG. 10. The repair person can then move to tower T3 and query the acoustic monitor on tower T3, which retrieves the logged event from the acoustic monitor on tower T3 (step 1020). With two logged events from two towers, the timestamps of the two logged events are compared (step 1030). The timestamps will indicate the event did not occur between towers T2 and T3 (step 1040=NO), so the next two towers are selected (step 1050). The event did not occur between the towers when the difference of their timestamps is the time it takes the sound of the event to travel between the two towers. The next two towers are towers T3 and T4. The repair person already has the logged event data from tower T3 (step 1010), so the repair person goes to tower T4 and queries the acoustic monitor on tower T4 to retrieve the logged event (step 1020). The timestamps are compared (step 1030). When the event is between these two towers (step 1040=YES), which is the case for the specific example in FIG. 11, the distance of the event from one or both of the towers is determined based on the time differential of the timestamps (step 1060). Once the location of the event is determined, the repair person can determine the best route to take to get to the event location to begin repairs.

Figures 12, 13, 14:
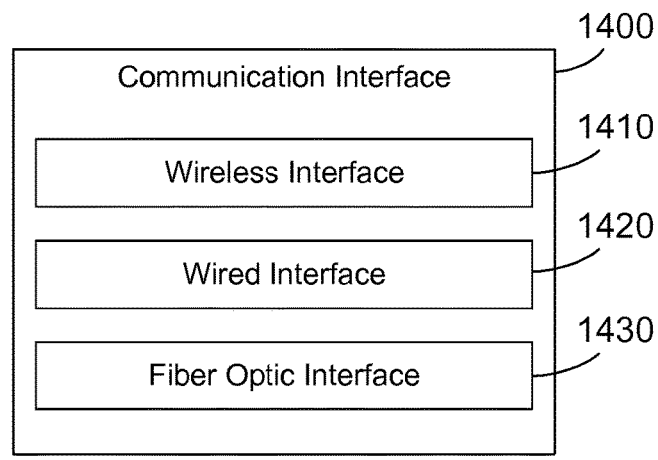
FIG. 12 shows an equation for computing differential distance of the event from the two towers.
FIG. 13 shows an equation for computing distance from one of the towers to the event.
FIG. 14 is a block diagram showing one suitable implementation for the communication interface 304 shown in FIG. 3.

FIG. 12 shows a formula that can be used to compute a distance representative of the time differential between the two towers that detected the event. TS1 and TS2 represent the timestamps of the respective events in the acoustic monitors on the two towers. The absolute value of the different between the two timestamps is computed. This absolute value is then multiplied by the nominal speed of sound in air, which is 343 meters per second (m/s). The result is a value in meters that reflects the differential between the two towers. The distance from a tower to the event is computed using the formula in FIG. 13. Note that A in FIG. 13 is the result computed in the equation in FIG. 12. The distance from the tower to the event is the total distance between the towers, less the computed value A from FIG. 12, with the result divided by two. The distance can then be compared to the timestamps, and the smaller distance will correspond to the earlier timestamp, while the larger distance will correspond to the later timestamp.

Figure 11:
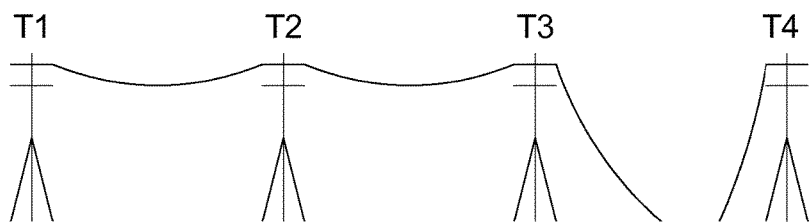
FIG. 11 is a diagram of a power transmission system to illustrate one example for method 1000 in FIG. 10.

A specific example is now provided to illustrate the use of the equations in FIGS. 12 and 13 to determine distance from the towers to the event. Let's assume the distance between towers in FIG. 11 is 500 meters. Let's also assume the break event was logged in the acoustic monitor for tower T3 with a timestamp of 23:11.8746, and was logged in the acoustic monitor for tower T4 with a timestamp of 23:11.5831. Using the equation in FIG. 12, the absolute value of the difference between the timestamps, namely 0.2915, is multiplied by 343 m/s, which results in 100 meters as value A in FIG. 12. This means one of the towers is 100 meters closer to the event than the other tower. Now plugging value A into the equation in FIG. 13, the distance from the tower to the event is the distance between towers of 500 meters less 100 meters, with the difference divided by two. The result is 200 meters. Because the distance between towers is 500 meters, and the result of 200 meters is less than half that distance, we known the result of 200 meters corresponds to the earlier timestamp, which corresponds to tower T4. Thus we know that the break is 200 meters from T4, which means the break is 300 meters from T3. With this knowledge, the repair person can determine the quickest way to access the break to begin repairs.

The communication interface 1400 shown in FIG. 14 is one suitable implementation of the communication interface 392 shown in FIG. 3. The disclosure and claims herein extend to any suitable way to communicate the logged event data to an external electronic device, typically a mobile device that is hand-held by a repair person. The communication interface 1400 may include a wireless interface 1410. In one implementation, the wireless interface 1410 is a local wireless interface, such as a Bluetooth interface, that allows a hand-held device to communicate with the acoustic monitor when in very close proximity. This could require, for example, the repair person to climb up a ladder or part way up a tower to get close enough to the acoustic monitor to establish a wireless connection. The wireless interface 1410 could additionally or alternatively include a WiFi interface that allows a hand-held device of the repair person to communicate with an acoustic monitor via WiFi, which allows much greater distance than a Bluetooth interface. This would eliminate the need for the repair person to climb a ladder or part of the tower. The wireless interface 1410 could additionally or alternatively include a cell phone interface that allows communicating via a cell phone network. While this may work in many locations in populated areas, this is not a viable option in more remote areas that do not have cell phone service. The wireless interface 1410 could additionally or alternatively include an interface that communicates on the utilities radio band, and may include encryption and remote login capability.

The communication interface 1400 could additionally or alternatively include a wired interface 1420. The wired interface 1420 could be any suitable wired interface, such as a wired connection on a TCP/IP local area network. The wired interface 1420 could include encryption and remote login capability. The communication interface 1400 could additionally or alternatively include a fiber optic interface 1430. The fiber optic interface 1430 could include encryption and remote login capability.

The ability to provide different communications interfaces allows great flexibility in designing a system to use the acoustic monitors. On the least sophisticated end of the spectrum, a simple wireless interface is provided that only supports on-site retrieval of event data using a hand-held device. A more sophisticated system would use towers in an urban area that have cell phone coverage, where the cell phone network provides the capability of remote login and querying of event data. A very sophisticated system could include a fiber optic connection to all the acoustic monitors on all the towers, thereby allowing a person at a remote location, such as an electrical control center, to remotely log in and query event data. In this type of sophisticated system, the location of an event could be accurately determined very quickly after the event occurred, which allows dispatching repair personnel to the location of the event to quickly get the power turned back on. Of course, any suitable combination of these could be used to create a hybrid mix of acoustic devices that communicate in different ways. The disclosure and claims herein expressly extend to any suitable way for the acoustic monitor to communicate its logged events, whether currently known or developed in the future.

Figure 15:
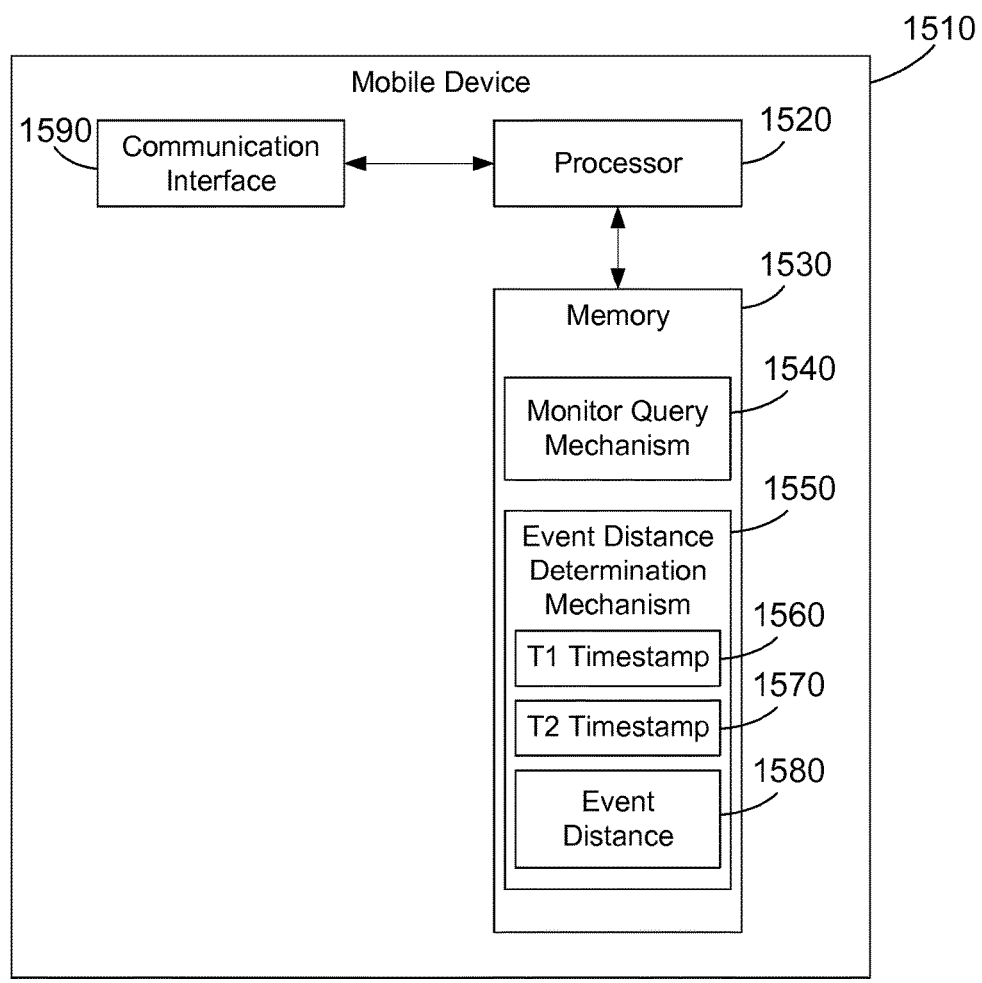
FIG. 15 is a block diagram of a mobile device that can communicate with the acoustic monitors on towers.

The querying of the acoustic monitors on the towers and the computation of distance to an event from one or both of the towers is preferably performed by a mobile electronic device external to the acoustic monitors. FIG. 15 shows a block diagram of a suitable portable device 1510 that is capable of performing method 1000 in FIG. 10. Mobile device 1510 includes a processor 1520, a memory 1530, and a communication interface 1590. The processor 1520 can be any suitable processor, as discussed above with reference to processor 320 in FIG. 3. The memory 1530 can be any suitable memory, as discussed above with reference to memory 330 in FIG. 3. The communication interface 1590 can be any suitable communication interface, as discussed above with reference to communication interface 1400 in FIG. 14. The memory 1530 preferably includes a monitor query mechanism 1540 that queries an acoustic monitor vie the communication interface 1590 and retrieves logged data corresponding to an event from the acoustic monitor via the communication interface 1590, as discussed above with reference to steps 1010 and 1020 in FIG. 10. An event distance determination mechanism 1550 receives a first timestamp of an event at a first tower 1560 and a second timestamp of the same event at a second tower 1570, and using these two timestamps determines an event distance 1580 that is the distance of the event from one or both of the two towers that have acoustic monitors that provided the T1 timestamp 1560 and the T2 timestamp 1570. The event distance determination mechanism 1550 preferably performs steps 1030, 1040 and 1060 in FIG. 10.

The mobile device 1510 could be a custom-designed device that is made specifically to communicate with the acoustic monitors. In the alternative, the mobile device 1510 could be a smart phone running a suitable app that implements the monitor query mechanism 1530 and the event distance determination mechanism 1550. Note that the disclosure herein includes not only the acoustic monitor, but also includes a method for acoustically detecting an event and a system that includes two or more acoustic monitors such as 310 shown in FIG. 3 and a mobile device such as 1510 shown in FIG. 15.

Figure 16:
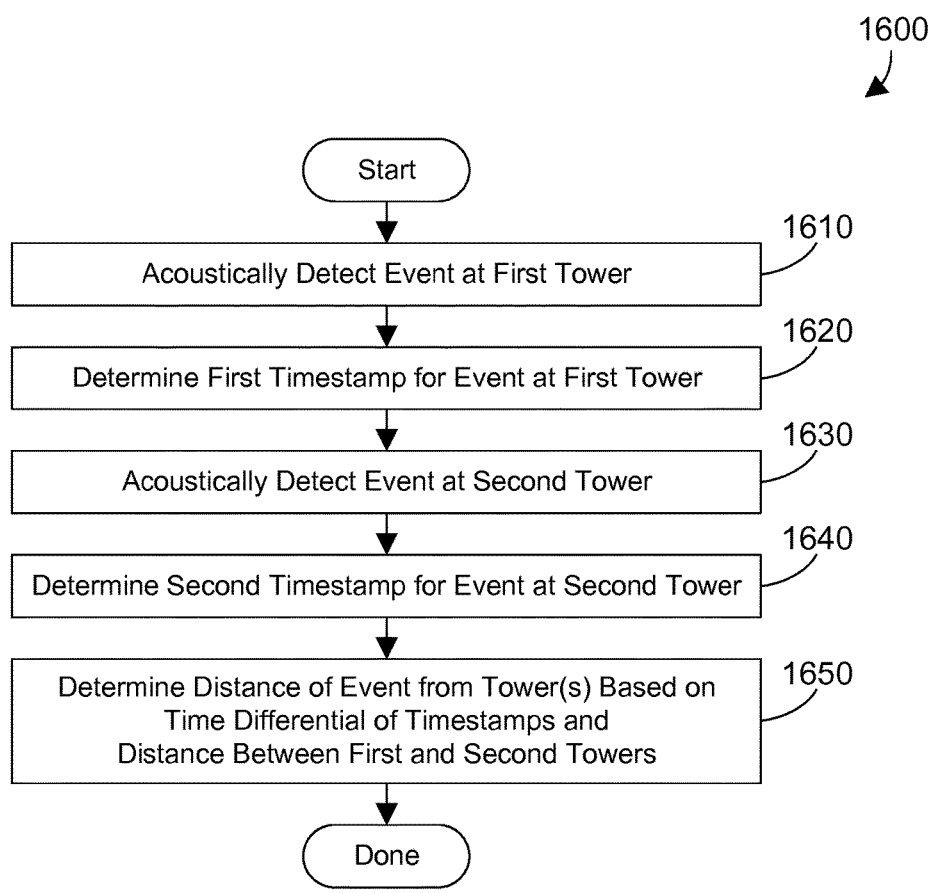
FIG. 16 is a flow diagram of a method for acoustically detecting an event a two towers and determining distance from one of both of the towers to the event.

Referring to FIG. 16, a method 1600 represents steps performed by the system that includes two or more acoustic monitors such as 310 in FIG. 3 and a mobile device such as 1510 shown in FIG. 15. Acoustically detect an event at a first tower (step 1610). Determine a first timestamp for the event at the first tower (step 1620). Acoustically detect the same event at a second tower (step 1630). Determine a second timestamp for the event at the second tower (step 1640). Then determine distance of the event from one or both towers based on the time differential of the timestamps and the distance between the first and second towers (step 1650). Method 1600 is then done.

The examples in FIGS. 2, 7 and 11 are directed to a particular type of event, namely a break of a power transmission line. Note, however, that the disclosure and claims herein expressly extend to any suitable event that can be detected by acoustic monitors, whether currently known and understood, or developed in the future. Examples of events that can be detected by acoustic monitors include: a lightning strike on a power transmission line mid-span that may result in a momentary short to ground; the beginning of a structural failure on the cable support that could cause different wind vibration modes on the power transmission line and on the tower, which could be detected via low frequency audio; the sound of a dropped or thrown chain or metal rod which attempted to short the power transmission line, but fell before the power transmission line broke; a gunshot from a vandal hitting the tower or cable; and an earthquake, tremor, mudslide, etc. which could be detected via infrasound due to the new vibrational patterns on the tower and power transmission line. In short, any event that can be detected acoustically could be detected by the acoustic monitors disclosed herein.

An acoustic monitor detects and logs events based on the acoustic characteristics of the event. The acoustic monitor is placed on a tower, and a baseline acoustic signature is established. Events can be defined by variance from the baseline, or by matching one of a set of predefined acoustic signatures. When an event is detected, the acoustic monitor logs the event. A repair person queries the acoustic monitors to narrow down where the event occurred to be between two towers, and can then query the acoustic monitors on those two towers. Using the timestamps of the event in each of the towers, and using the known speed of sound in air, the repair person can quickly calculate the location of the event from both towers. By knowing the location of the event, the repair person knows exactly how to quickly access the location to make the needed repairs.

One skilled in the art will appreciate that many variations are possible within the scope of the claims. Thus, while the disclosure is particularly shown and described above, it will be understood by those skilled in the art that these and other changes in form and details may be made therein without departing from the spirit and scope of the claims.

The invention claimed is:

1. A system for detecting location of an event for a power transmission line comprising:
    (A) on a first tower that supports the power transmission line, a first acoustic monitor comprising:
        a first processor;
        a first memory coupled to the first processor;
        a first acoustic transducer coupled to the first processor;
        a first time clock coupled to the first processor;
        a first acoustic monitor mechanism residing in the first memory and executed by the first processor that monitors data from the first acoustic transducer, detects when an event occurs based on the monitored data, and logs first data corresponding to the event and a first timestamp from the first time clock corresponding to the event; and
        a first communication interface;
    (B) on a second tower that supports the power transmission line, a second acoustic monitor comprising:
        a second processor;
        a second memory coupled to the second processor;
        a second acoustic transducer coupled to the second processor;
        a second time clock coupled to the second processor;
        a second acoustic monitor mechanism residing in the second memory and executed by the second processor that monitors data from the second acoustic transducer, detects when the event occurs based on the monitored data, and logs second data corresponding to the event and a second timestamp from the second time clock corresponding to the event; and
        a second communication interface;
    (C) a portable device comprising:
        a third communication interface that communicates with the first communication interface in the first acoustic monitor and communicates with the second communication interface in the second acoustic monitor;
        an event distance determination mechanism that determines distance from at least one of the first and second towers to the event by:
            sending a request from the third communication interface to the first communication interface, and in response thereto, the first acoustic monitor sends the first data and the first timestamp corresponding to the event via the first communication interface to the third communication interface;
            sending a request from the third communication interface to the second communication interface, and in response thereto, the second acoustic monitor sends the second data and the second timestamp corresponding to the event via the second communication interface to the third communication interface; and determining distance from at least one of the first and second towers to the event from the first timestamp and the second timestamp.

2. The system of claim 1 wherein the portable device comprises a cell phone running an app that provides the event distance determination mechanism.

3. The system of claim 1 wherein the event comprises a break in the power transmission line.

* * * * *